US00PP11250P

United States Patent [19]

Rother

[11] Patent Number: Plant 11,250

[45] Date of Patent: Feb. 29, 2000

[54] HELICHRYSUM PLANT NAMED 'LEMON BUSH'

[76] Inventor: Reinhard W. Rother, 56 Emerald Monbulk Road, Emerald, Victoria, 3782, Australia

[21] Appl. No.: 08/977,481

[22] Filed: Nov. 24, 1997

[51] Int. Cl.[7] ..... A01H 5/00

[52] U.S. Cl. ..... Plt./359

[58] Field of Search ..... Plt./68.1, 359

[56] References Cited

U.S. PATENT DOCUMENTS

P.P. 9,666 10/1996 Bautista ..... Plt./68.1

*Primary Examiner*—Howard J. Locker
*Assistant Examiner*—Kent L. Bell
*Attorney, Agent, or Firm*—C. A. Whealy

[57] ABSTRACT

A distinct cultivar of Helichrysum plant named 'Lemon Bush', characterized by mostly upright growth habit when plants are young becoming more outwardly spreading with development; freely branching and bushy, dense growth; vigorous growth rate; numerous long-lasting large inflorescences; and attractive bright yellow involucral bracts and orange disc florets.

1 Drawing Sheet

The present invention relates to a new and distinct cultivar of Helichrysum plant, botanically known as *Helichrysum bracteatum,* and hereinafter referred to by the cultivar name 'Lemon Bush'.

The new cultivar is a product of a planned breeding program conducted by the inventor in Emerald, Victoria, Australia. The objective of the breeding program was to create new Helichrysum cultivars with interesting and unique inflorescence colors.

The new cultivar originated from a cross made by the inventor of a nonpatented yellow-flowered selection of *Helichrysum bracteatum* as the male or pollen parent with the inventor's proprietary *Helichrysum bracteatum* selection No. 93/202 as the female or seed parent.

The cultivar 'Lemon Bush' was discovered and selected in 1994 by the inventor as a flowering plant within the progeny of the stated cross in a controlled environment in Emerald, Victoria, Australia. The selection of the new Helichrysum was based on its unique and attractive floret colors and desirable growth habit.

Asexual reproduction of the new cultivar by terminal cuttings taken at Emerald, Victoria, Australia, has shown that the unique features of this new Helichrysum are stable and reproduced true to type in successive generations.

The cultivar 'Lemon Bush' has not been observed under all possible environmental conditions. The phenotype may vary somewhat with variations in environment such as temperature, light intensity, and fertility level, without, however, any variance in genotype.

The following traits have been repeatedly observed and are determined to be the unique characteristics of 'Lemon Bush'. These characteristics in combination distinguish 'Lemon Bush' as a new and distinct cultivar:

1. Young plants are mostly upright, growth habit becomes more outwardly spreading as plants develop.
2. Freely branching and bushy, dense growth.
3. Vigorous growth rate.
4. Numerous large inflorescences that last at least five weeks.
5. Attractive inflorescences with bright yellow involucral bracts contrasted with orange disc florets.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. The top photograph comprises a top perspective view of a typical potted plant of the cultivar 'Lemon Bush'. The bottom photograph comprises a close-up view of typical inflorescences of a plant of the cultivar 'Lemon Bush'. Flower and foliage colors in the photographs may appear different than the actual colors due to light reflectance.

DETAILED BOTANICAL DESCRIPTION

The following observations and measurements describe plants grown during the spring and summer in Encinitas, Calif. under full sun with day and night temperatures averaging 24° and 16° C., respectively. Color references are made to The Royal Horticultural Society Colour Chart except where general terms of ordinary dictionary significance are used.

Botanical classification: *Helichrysum bracteatum* cultivar 'Lemon Bush'.

Parentage:

*Male, or pollen, parent.*—Yellow-flowered *Helichrysum bracteatum* selection (not patented).

*Female or seed, parent.*—*Helichrysum bracteatum* proprietary selection No. 93/202 (not patented).

PROPAGATION:

*Type.*—By cuttings.

*Time to initiate roots.*—About 14 days at temperatures of 20° C.

*Time to develop roots.*—25 to 28 days at temperatures of 20 to 25° C.

*Rooting habit.*—Vigorous, fibrous and thick.

Plant description:

*Form.*—Young plants are mostly upright, growth habit becomes more outwardly spreading as plants develop; herbaceous annual, may be perennial in warm climates.

*Branching habit.*—Freely branching, very dense and bushy.

*Plant height.*—About 45 cm.

*Plant diameter.*—About 68 cm.

*Vigor.*—Vigorous.

*Lateral stem description.*—Internode length: About 1.5 cm. Diameter: About 4 mm. Texture: Fine white hairs, hirsute. Color: 144B.

*Foliage description.*—Leaves single, alternate and generally symmetrical. Foliage durable. Length: About 15.5 cm. Width: About 3 cm. Shape: Linear, acuminate apex and sessile. Margin: Entire. Texture: Both surfaces covered with very fine white hairs. Leaves soft, pliable. Color: Young leaves, upper surface: 147A. Young leaves, lower surface: 147B. Mature leaves, upper surface: 147A. Mature leaves, lower surface: 147B. Venation, upper surface: 147A, sunken. Venation, lower surface: 146A, prominent midvein.

Flower description:

*Flower type and habit.*—Single daisy-type composite inflorescence form. Involucral bracts and disc florets arranged acropetally on a capitulum. Inflorescences persistent. Inflorescences orientated perpendicular to stem.

*Quantity of inflorescences.*—Freely flowering with numerous inflorescences per plant. Inflorescences formed at terminals with one per terminal.

*Natural flowering season.*—Natural flowering season is spring to early fall. Plants flower continuously during this period.

*Fragrance.*—Very faint.

*Inflorescence diameter.*—About 6.5 cm.

*Inflorescence depth (height).*—About 2 cm.

*Receptacle diameter.*—About 1.75 cm.

*Receptacle depth (height).*—About 5 mm.

*Involucral bracts.*—Appearance: Straw-like, tough, dry. Aspect: Cupped. Quantity: About 100 per inflorescence. Shape: Subulate, narrow triangle. Apex: Acute. Base: Truncate, involucral bracts bent at an acute angle at base. Margin: Entire. Length: About 2.5 cm with green (147A) base of 5 mm. Width: About 9 mm. Color: When opening, upper surface: 3B. When opening, lower surface: 3C. Mature, upper surface: 3A/3B. Mature, lower surface: 3B/3C.

*Disc florets.*—Shape: Tubular, fluted at apex and heavily whiskered at base. Diameter of disc: About 1.9 cm. Disc floret length: About 1 cm. Disc floret width: About 1 mm. Color: Immature: 154A to 3A. Mature: More intense than 23A. Number of disc florets per inflorescence: Numerous, at least 300 per inflorescence.

*Sepals.*—Shape: Linear with acute apex. Margin: Entire. Texture: Pubescent, fine white hairs. Color: 147A.

*Peduncle.*—Length: 12.5 cm. Strength: Strong, but flexible. Texture: Covered with fine white hairs. Color: 144A.

*Flower bud.*—Shape: Conical. Length: About 2.5 cm. Diameter: About 2 cm. Color: 3C.

*Androecium.*—Anther color: 23A. Pollen color: 23A. Amount of pollen: Abundant.

*Gynoecium.*—Present.

Disease resistance: The new Helichrysum has been not been observed to be more resistant to pathogens common to Helichrysums.

Seed production: Seed production has not been observed.

It is claimed:

1. A new and distinct cultivar of Helichrysum plant named 'Lemon Bush', as illustrated and described.

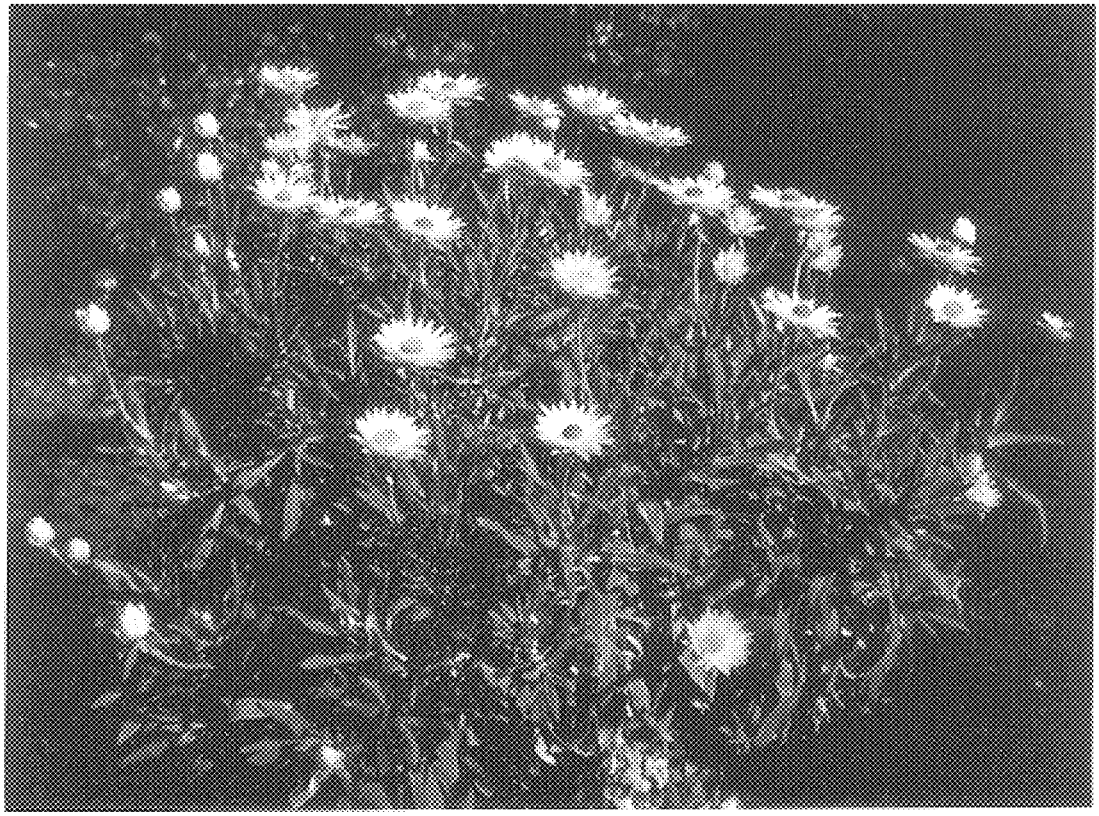
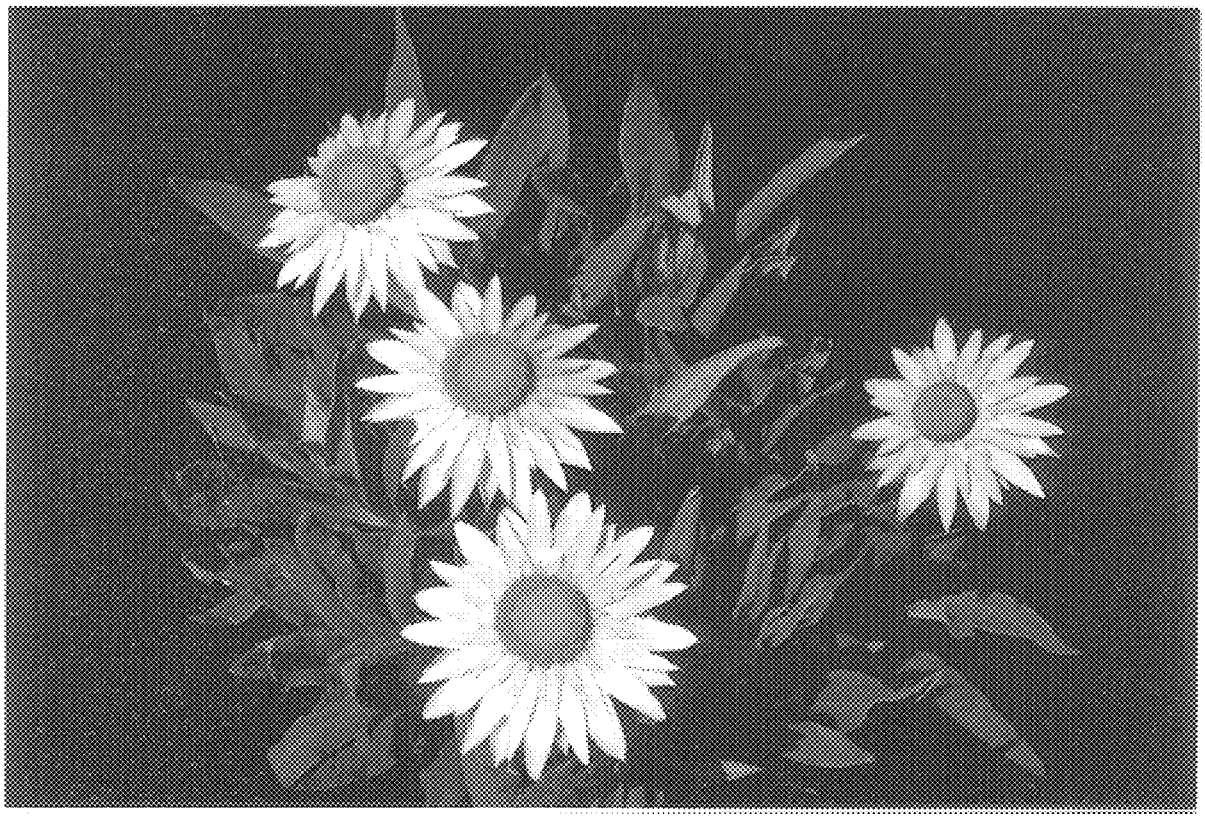

* * * * *